United States Patent [19]

Timmler et al.

[11] 4,349,556
[45] Sep. 14, 1982

[54] PESTICIDALLY ACTIVE 1-ACYLOXY-1-PHENYL-2-AZOLYL-ETHANES

[75] Inventors: Helmut Timmler; Wolfgang Krämer; Karl H. Büchel, all of Wuppertal; Wilhelm Brandes, Cologne; Paul-Ernst Frohberger; Bernhard Homeyer, both of Leverkusen, all of Fed. Rep. of Germany

[73] Assignee: Bayer Aktiengesellschaft, Leverkusen, Fed. Rep. of Germany

[21] Appl. No.: 804,832

[22] Filed: Jun. 8, 1977

[30] Foreign Application Priority Data

Jun. 24, 1976 [DE] Fed. Rep. of Germany ....... 2628419
Jun. 24, 1976 [DE] Fed. Rep. of Germany ....... 2628420

[51] Int. Cl.$^3$ ................. A01N 43/50; A01N 43/64; C07D 233/60; C07D 249/08
[52] U.S. Cl. ................. 424/269; 424/273 R; 424/232; 548/262; 548/341
[58] Field of Search ................. 548/341; 260/308 R; 424/269, 273

[56] References Cited

U.S. PATENT DOCUMENTS

| 3,755,349 | 8/1973 | Timmler et al. | 260/308 R |
| 3,892,764 | 7/1975 | Metzger et al. | 548/341 |
| 4,005,083 | 1/1977 | Büchel et al. | 260/299 |
| 4,038,409 | 7/1977 | Walker et al. | 424/273 |
| 4,315,016 | 2/1982 | Balasubramanyan et al. | 548/262 |

FOREIGN PATENT DOCUMENTS 2431407  1/1976  Fed. Rep. of Germany ... 260/308 R
2640823  3/1977  Fed. Rep. of Germany ...... 548/262

OTHER PUBLICATIONS

Burger, Medicinal Chemistry, (Second Edition, New York, 1960), pp. 1051–1053.
Timmler et al., Chemical Abstracts, vol. 84, Abstract No. 150636k (1976).

Primary Examiner—Alton D. Rollins
Attorney, Agent, or Firm—Sprung, Horn, Kramer & Woods

[57] ABSTRACT

1-Acyloxy-1-phenyl-2-azolyl-ethanes of the formula

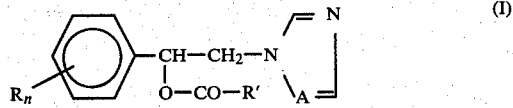

in which
R represents halogen, alkyl, alkoxy, alkylthio, alkylsulphonyl, haloalkyl, nitro, cyano, optionally substituted phenyl or optionally substituted phenoxy,
R' represents alkyl, alkenyl, alkynyl, cycloalkyl, haloalkyl, optionally substituted phenyl, optionally substituted phenylalkyl, optionally substituted phenoxyalkyl, amino, alkylamino, dialkylamino, alkylalkyl-carbonylamino or optionally substituted phenylamino,
A represents a CH-group or a nitrogen atom, and
n represents 0, 1, 2, 3, 4 or 5, or salts thereof, which possess fungicidal, bactericidal and nematicidal properties.

16 Claims, No Drawings

PESTICIDALLY ACTIVE 1-ACYLOXY-1-PHENYL-2-AZOLYL-ETHANES

The present invention relates to and has for its objects the provision of particular new 1-acyloxy-1-phenyl-2-azolylethanes and salts thereof which possess insecicidal, acaricidal and nematicidal properties, active compositions in the form of mixtures of such compounds with solid and liquid dispersible carrier vehicles, and methods for producing such compounds and for using such compounds in a new way especially for combating pests, e.g. fungi, bacteria and nematodes, with other and further objects becoming apparent from a study of the within specification and accompanying examples.

It has been disclosed in German Published Specification DOS No. 2,063,857 that 1-[β-alkoxy-β-aryl)-ethyl]-imidazoles, for example 1-β-butoxy-β-(4'-chlorophenyl)-ethyl]-imidazole 1,5-naphthalene disulphonic acid salt (Compound A), exhibit a good fungicidal activity. Their action is, however, not always fully satisfactory, especially when low amounts and low concentrations are used. Furthermore, it has been generally known for a considerable time that zinc ethylene-1,2-bis-dithiocarbamate (Compound B) is a good agent for combating fungal diseases of plants (see Phystopathology 33, 1,113 (1963)). However, its use as a seed dressing is only possible within certain limitations, since its action is poor when low amounts and low concentrations are used.

The present invention provides compounds which are 1-acyloxy-1-phenyl-2-azolyl-ethanes or salts thereof, the 1-acyloxy-1-phenyl-2-azolyl-ethanes being of the general formula

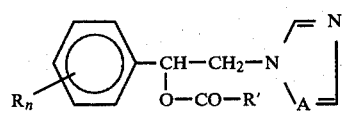

in which
R represents halogen, alkyl, alkoxy, alkylthio, alkylsulphonyl, haloalkyl, nitro, cyano, optionally sub-substituted phenyl or optionally substituted phenoxy,
R' represents alkyl, alkenyl, alkynyl, cycloalkyl, haloalkyl, optionally substituted phenyl, optionally substituted phenylakyl, optionally substituted phenoxyalkyl, amino, alkylamino, dialkylamino, alkyl-alkyl-carbonylamino or optionally substituted phenylamino,
A represents a CH-group or a nitrogen atom, and
n represents 0, 1, 2, 3, 4 or 5.

These compounds have been found to exhibit powerful fungicidal and nematocidal properties.

It is generally advantageous in practice, if the compounds are to be used in the form of salts, that these should be physiologically tolerated salts (from the point of view of phytotoxicity). Such salts are of course generally those with physiologically tolerated acids.

Preferably, R represents halogen (especially fluorine, chlorine or bromine), nitro, cyano, alkyl or alkylsulphonyl each with 1 to 4 carbon atoms, alkoxy or alkylthio each with 1 or 2 carbon atoms, haloalkyl with up to 4 carbon atoms and up to 5 halogen atoms (especially haloalkyl with up to 2 carbon atoms and up to 3 identical or different halogen atoms, preferred halogens being fluorine and chlorine; trifluoromethyl may be mentioned as an example of such haloalkyl), or phenyl or phenoxy, either of which is optionally substituted by halogen (especially fluorine, chlorine or bromine), cyano, nitro or haloalkyl with 1 or 2 carbon atoms and up to 3 identical or different halogen atoms (preferred halogens being fluorine and chlorine; trifluoromethyl may be mentioned as an example of such a substituent);
R' represents straight-chain or branched alkyl with 1 to 6 (especially 1 to 4) carbon atoms, straight-chain or branched alkenyl or alkynyl each with 2 to 4 carbon atoms, haloalkyl with 1 or 2 carbon atoms and 1 to 5 halogen atoms (especially fluorine and chlorine), cycloalkyl with 5 to 7 carbon atoms, (especially cyclohexyl), phenylalkyl or phenoxyalkyl, each with 1 or 2 carbon atoms in the alkyl moiety, or phenyl, such phenylalkyl or phenoxyalkyl or phenyl being optionally substituted in the phenyl by halogen, amino, cyano, nitro or alkyl with 1 or 2 carbon atoms, or represents amino, alkylamino or dialkylamino or alkyl-alkyl-carbonylamino each with 1 to 4 (especially 1 or 2) carbon atoms in each alkyl moiety, or phenylamino which is optionally substituted by halogen, nitro or cyano; and n represents 0, 1, 2 or 3.

Surprisingly, the compounds of the invention exhibit a substantially greater fungicidal activity, especially against species of rust and mildew, than the known 1-[β-alkoxy-β-arylethyl]-imidazoles, for example 1-[β-butoxy-β-(4'-chlorophenyl)-ethyl]-imidazole, which are the most closely related compounds, both chemically and in respect of their action or than the known zinc ethylene-1,2-bis-dithiocarbamate a compound of the same type of action. The additional nematocidal action of the compounds of the invention, which is superior to the action of 1-[β-butoxy-β-(4'-chlorophenyl)ethyl]-imidazole, is also surprising. The active compounds according to the invention thus represent an enrichment of the art.

The invention also provides a process for the production of a compound according to the invention in which a 1-hydroxy-1-phenyl-2-azolyl-ethane of the general formula

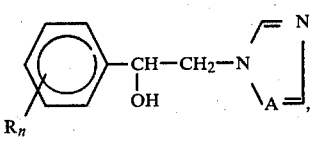

in which
R, A and n have the above-mentioned meanings, is reacted
(a) with an acid halide of the general formula

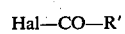

in which
R' has the above-mentioned meaning and
Hal represents halogen, preferably chlorine or bromine,
in the presence of a solvent and optionally in the presence of an acid-binding agent, or
(b) with an acid anhydride of the general formula

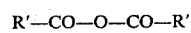

in which
R' has the above-mentioned meaning, in the presence of a solvent and optionally in the presence of a catalyst, or (c) with a ketone of the general formula $$O=C=CH-R''\qquad (V),$$

in which

R'' represents hydrogen, alkyl, alkenyl, alkynyl or halomethyl, in the presence of a solvent, or (d) with an isocyanate of the general formula $$O=C=N-R'''\qquad (VI),$$

in which

R''' represents alkyl or optionally substituted phenyl, in the presence of a solvent and optionally in the presence of a catalyst.

If the 1-acyloxy-1-phenyl-2-azolyl-ethanes are initially obtained as such, they can of course be converted, if desired, into salts by reaction with acids.

If 1-(2,4-dichlorophenyl)-1-hydroxy-2-(1,2,4-triazol-1-yl)-ethane and acetyl chloride are used as starting materials, the course of the reaction can be represented by the following formula scheme (process variant (a)):

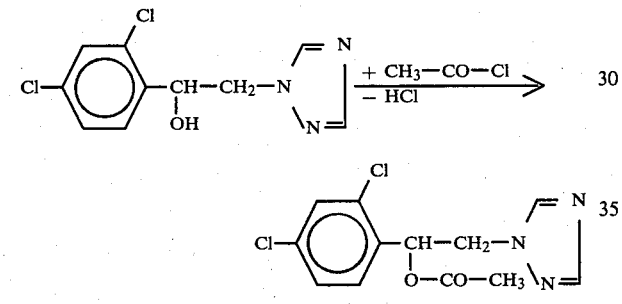

If 1-(2,4-dichlorophenyl)-1-hydroxy-2-(1,2,4-triazol-1-yl)-ethane and acetic anhydride are used as starting materials, the course of the reaction can be represented by the following formula scheme (process variant (b)):

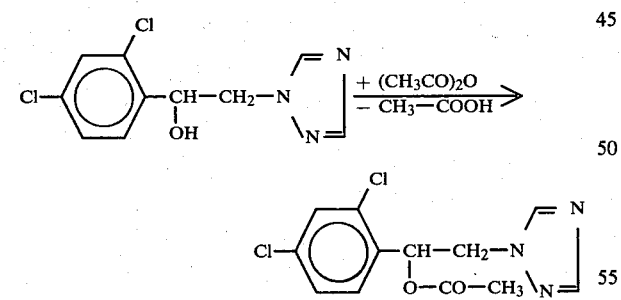

If 1-(2,4-dichlorophenyl)-1-hydroxy-2-(1,2,4-triazol-1-yl)-ethane and methyl-ketone are used as starting materials, the course of the reaction can be represented by the following formula scheme (process variant (c)):

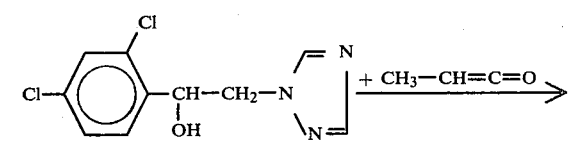

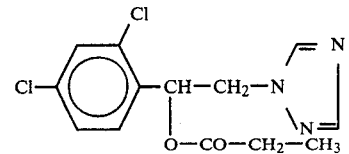

If 1-(2,4-dichlorophenyl)-1-hydroxy-2-(imidazol-1-yl)-ethane and 4-chlorophenyl isocyanate are used as starting materials, the course of the reaction can be represented by the following formula scheme (process variant (d)):

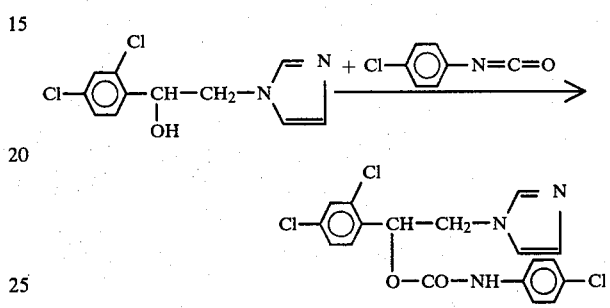

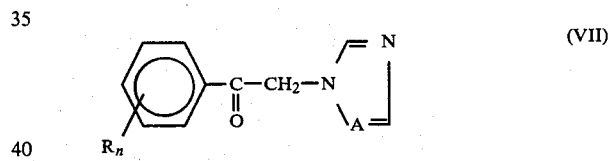

1-Hydroxy-1-phenyl-2-azolyl-ethanes of the formula (II) are known (see German Offenlegungsschriften (German Published Specifications) Nos. 2,431,407 and 2,063,857) and can easily be prepared in accordance with the processes described there. Such compounds may be obtained by reducing the corresponding azolylalkanones of the general formula

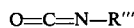 (VII)

in which R, A and n have the above-mentioned meanings, by means of aluminum isopropylate, or with formamidinesulphinic acid and alkali metal hydroxide, or with complex hydrides.

The following are examples of 1-hydroxy-1-phenyl-2-imidazolyl-ethanes of the formula (II): 1-(4-chlorophenyl)-1-hydroxy-2-(imidazol-1-yl)-ethane, 1-(2,4-dichlorophenyl)-1-hydroxy-2-(imidazol-1-yl)-ethane, 1-(3-chlorophenyl)-1-hydroxy-2-(imdazol-1-yl)-ethane, 1-(4-fluorophenyl)-1-hydroxy-2-(imidazol-1-yl)-ethane, 1-(4-methylphenyl)-1-hydroxy-2-(imidazol-1-yl)-ethane, 1-(3-trifluoromethylphenyl)-1-hydroxy-2-(imidazol-1-yl)-ethane, 1-(4-methoxyphenyl)-1-hydroxy-2-(imidazol-1-yl)-ethane, 1-(3,4-dichlorophenyl)-1-hydroxy-2-(imidazol-1-yl)-ethane, 1-[-(4'-chlorobiphenylyl)]-1-hydroxy-2-(imidazol-1-yl)-ethane, 1-[4-(4'-chlorophenoxy)-phenyl]-1-hydroxy-2-(imidazol-1-yl)-ethane, 1-(4-biphenylyl)-1-hydroxy-2-(imidazol-1-yl)-ethane, 1-(4-phenoxyphenyl)-1-hydroxy-2-(imidazol-1-yl)-ethane, 1-phenyl-1-hydroxy-2-(imidazol-1-yl)-ethane, 1-(2-ethylphenyl)-1-hydroxy-2-(imidazol-1-yl)-ethane, 1-(4-chloro-2-methylphenyl)-1-hydroxy-2-(imidazol-1-yl)-ethane, 1-(4-trifluoromethylphenyl)-1-hydroxy-2-(imidazol-1-yl)-ethane, 1-(4-nitrophenyl)-1-hydroxy-2-(imidazol-1-yl)-ethane, 1-(2-fluorophenyl)-1-hydroxy-2-(imidazol-1-yl)-ethane, 1-(2-chlorophenyl)-1-hydroxy-2-(imidazol-1-yl)-ethane, 1-

(4-bromophenyl)-1-hydroxy-2-(imidazol-1-yl)-ethane, 1-(4-cyanophenyl)-1-hydroxy-2-(imidazol-1-yl)-ethane, 1-(2-methoxyphenyl)-1-hydroxy-2-(imidazol-1-yl)-ethane, 1-(2-ethylthiophenyl)-1-hydroxy-2-(imidazol-1-yl)-ethane, 1-(4-methylsulphonylphenyl)-1-hydroxy-2-(imidazol-1-yl)ethane, 1-(2,4,5-trichlorophenyl)-1-hydroxy-2-(imidazol-1-yl)-ethane, 1-[4-(2',4'-dichlorobiphenylyl)]-1-hydroxy-2-(imidazol-1-yl)-ethane and 1-[4-(2',4'-dichlorophenoxy)phenyl]-1-hydroxy-2-(imidazol-1-yl)-ethane.

The following are examples of 1-hydroxy-1-phenyl-2-triazolyl-ethanes of the formula (II): 1-(4-chlorophenyl)-1-hydroxy-2-(1,2,4-triazol-1-yl)-ethane, 1-(2,4-dichlorophenyl)-1-hydroxy-2-(1,2,4-triazol-1-yl)-ethane, 1-(3-chlorophenyl)-1-hydroxy-2-(1,2,4-triazol-1-yl)-ethane, 1-(4-fluorophenyl)-1-hydroxy-2-(1,2,4-triazol-1-yl)-ethane, 1-(4-methylphenyl)-1-hydroxy-2-(1,2,4-triazol-1-yl)-ethane, 1-(3-trifluoromethylphenyl)-1-hydroxy-2-(1,2,4-triazol-1-yl)-ethane, 1-(4-methoxyphenyl)-1-hydroxy-2-(1,2,4-triazol-1-yl)-ethane, 1-(3,4-dichlorophenyl)-1-hydroxy-2-(1,2,4-triazol-1-yl)-ethane, 1-[4-(4'-chlorobiphenylyl)]-1-hydroxy-2-(1,2,4-triazol-1-yl)-ethane, 1-[4-(4'-chlorophenoxy)phenyl]-1-hydroxy-2-(1,2,4-triazol-1-yl)-ethane, 1-(4-biphenylyl)-1-hydroxy-2-(1,2,4-triazol-1-yl)-ethane, 1-(4-phenoxyphenyl)-1-hydroxy-2-(1,2,4-triazol-1-yl)-ethane, 1-phenyl-1-hydroxy-2-(1,2,4-triazol-1-yl)-ethane, 1-(2-ethylphenyl)-1-hydroxy-2-(1,2,4-triazol-1-yl)-ethane, 1-(4-chloro-2-methylphenyl)-1-hydroxy-2-(1,2,4-triazol-1-yl)-ethane, 1-(4-trifluoromethylphenyl)-1-hydroxy-2-(1,2,4-triazol-1-yl)-ethane, 1-(4-nitrophenyl)-1-hydroxy-2-(1,2,4-triazol-1-yl)-ethane, 1-(2-fluorophenyl)-1-hydroxy-2-(1,2,4-triazol-1-yl)-ethane, 1-(2-chlorophenyl)-1-hydroxy-2-(1,2,4-triazol-1-yl)-ethane, 1-(4-bromophenyl)-1-hydroxy-2-(1,2,4-triazol-1-yl)-ethane, 1-(4-cyanophenyl)-1-hydroxy-2-(1,2,4-triazol-1-yl)-ethane, 1-(2-methoxyphenyl)-1-hydroxy-2-(1,2,4-triazol-1-yl)-ethane, 1-(2-ethylthiophenyl)-1-hydroxy-2-(1,2,4-triazol-1-yl)-ethane, 1-(4-methylsulphonylphenyl)-1-hydroxy-2-(1,2,4-triazol-1-yl)-ethane, 1-(2,4,5-trichlorophenyl)-1-hydroxy-2-(1,2,4-triazol-1-yl)-ethane, 1-[4-(2',4'-dichlorobiphenylyl)]-1-hydroxy-2-(1,2,4-triazol-1-yl)-ethane and 1-[4-(2',4'-dichlorophenoxy)-phenyl]-1-hydroxy-2-(1,2,4-triazol-1-yl)-ethane.

Acid halides of the formula (III) are known and can be prepared in accordance with customary processes, for example by reacting carboxylic acids or their alkali metal salts with acid halides of phosphorus or sulphur. These methods are known from the general textbooks of organic chemistry. Examples of the acid halides are: acetyl chloride, acetyl bromide, propionic acid chloride, n-butyric acid chloride, i-butyric acid chloride, acrylic acid chloride, acrylic acid bromide, crotonic acid chloride, methacrylic acid chloride, vinylacetic acid chloride, chloroacetic acid chloride, carbamoyl chloride, dimethylcarbamoyl chloride, acetylcarbamoyl chloride, acetyl-methyl-carbamoyl chloride, α-chloropropionic acid chloride, trimethylacetic acid chloride, trimethylacetic acid bromide, benzoyl chloride, 4-chlorobenzoyl chloride, 2,4-dichlorobenzoyl chloride, phenylacetic acid chloride, 4-chlorophenylacetic acid chloride and 2,4-dichlorophenylacetic acid chloride.

Acid anhydrides of the formula (IV) required for process variant (b) are known and can be prepared in accordance with generally known processes, for example by the action of acid chlorides on the alkali metal salts of the carboxylic acids. Examples of the acid anhydrides are: acetic anhydride, propionic anhydride, butyric anhydride, acrylic anhydride, methacrylic anhydride, vinylacetic anhydride, chloroacetic anhydride, trimethylacetic anhydride, benzoic anhydride, 4-chlorobenzoic anhydride, 2,4-dichlorobenzoic anhydride, phenylacetic anhydride, 4-chlorophenylacetic anhydride and 2,4-dichlorophenylacetic anhydride.

The ketenes required for process variant (c) are generally defined by the formula (V). Herein R" preferably represents hydrogen, alkyl with 1 to 5 (especially 1 to 3) carbon atoms, alkenyl or alkynyl each with up to 3 carbon atoms or, preferably, halomethyl with 1 to 3 halogen atoms, especially fluorine and chlorine.

Such ketones are mostly known and can be prepared in accordance with known processes, for example by thermolysis of ketones or by dehydration of carboxylic acids (see Houben-Weyl, "Methoden der organischen Chemie" ("Methods of Organic Chemistry"), volume 7/4, Georg Thieme Verlag, Stuttgart).

The isocyanates for process variant (d) are generally defined by the formula (VI). In this formula, R''' preferably represents alkyl with 1 to 4 (especially 1 or 2) carbon atoms, or optionally substituted phenyl, wherein halogen, nitro and cyano are the preferred substituents.

Such isocyanates are known and can be prepared in accordance with generally customary processes, for example by reaction of amines with phosgene and subsequent heating. Such processes are known from the general textbooks of organic chemistry. Examples of the isocyanates are: methyl isocyanate, ethyl isocyanate, isopropyl isocyanate, tert.-butyl isocyanate, phenyl isocyanate, 4-chlorophenyl isocyanate, 2,4-dichlorophenyl isocyanate and 4-nitrophenyl isocyanate.

As mentioned above, the salts of the compounds of the formula (I) are often salts with physiologically tolerated acids. Preferred examples of such acids include the hydrogen halide acids (for example hydrobromic acid and especially hydrochloric acid), phosphoric acid, nitric acid, monofunctional and bifunctional carboxylic acids and hydroxycarboxylic acids (for example acetic acid, maleic acid, succinic acid, fumaric acid, tartaric acid, citric acid, salicyclic acid, sorbic acid and lactic acid) and 1,5-naphthalenedisulphonic acid.

The salts of the compounds of the formula (I) can be obtained in a simple manner in accordance with customary methods of forming salts, for example by dissolving the base (I) in ether, for example diethyl ether, and adding the acid, for example phosphoric acid, and the salts can be isolated in known manner, for example by filtering off, and can be purified if required.

Suitable solvents for the reaction of process variant (a) include all inert organic solvents. Preferred solvents include ketones, for example diethyl ketone and especially acetone and methyl ethyl ketone; nitriles, for example propionitrile and especially acetonitrile; ethers, for example tetrahydrofuran and dioxane; esters, for example ethyl acetate; aromatic hydrocarbons, for example benzene and toluene; and halogenated hydrocarbons, for example methylene chloride, carbon tetrachloride and chloroform.

Process variant (a) can optionally be carried out in the presence of an acid-binding agent (hydrogen halide acceptor); all customary acid-binding agents can be used for this purpose. They include organic bases, preferably tertiary amines, for example triethylamine, and also inorganic bases, for example alkali metal hydroxides and alkali metal carbonates.

The compounds of the formula (II) can if desired be employed in the form of their alkali metal ethanolates. A number of such ethanolates are described in application Ser. No. 729,935, filed Oct. 6, 1976 now pending. They are obtained by reacting the corresponding 1-hydroxy-1-phenyl-2-azolyl-ethanes with suitable strong bases, such as alkali metal amides or alkali metal hydrides, in an inert solvent. Examples are the sodium alcoholates of the 1-hydroxy-1-phenyl-2-triazolyl-ethanes and 1-hydroxy-1-phenyl-2-imidazolyl-ethanes which have been listed hereinabove as examples of compounds of formula (II).

In carrying out process variant (a), the reaction temperatures can be varied within a substantial range. In general, the reaction is carried out at 0° to 120° C., preferably 20° to 100° C.

When carrying out process variant (a), preferably 1 to 2 moles of halide of the formula (III) are employed per mole of the compound of the formula (II).

The compounds of the formula (I) are generally obtained in the form of their hydrohalides and can be isolated as such by precipitating them by adding an organic solvent, for example hexane, filtering off and purifying them, if appropriate, by recrystallization. The compounds of the formula (I) can also be isolated in the form of their free bases, by adding aqueous sodium bicarbonate solution to the reaction mixture and isolating the base in accordance with customary methods.

According to a preferred embodiment of process variant (a), the procedure followed is, advantageously, to start from a 1-hydroxy-1-phenyl-2-azolyl-ethane derivative and—as stated above—to convert the latter, in a suitable inert solvent, by means of an alkali metal hydride or alkali metal amide, to the alkali metal alkanolate, the latter being reacted immediately, without isolating it, with a halide of the formula (III), whereby the compounds according to the invention may be obtained in a single process step, with elimination of alkali metal halide.

Suitable solvents for the reaction of process variant (b) include all inert organic solvents. Preferred solvents include the solvents mentioned above in connection with process variant (a). Alternatively, an excess of the acid anhydride of the formula (IV) can be used as the solvent.

Catalysts which can be used in process variant (b) include all customary acid and basic catalysts, for example sulphuric acid, hydrochloric acid, hydrobromic acid, boron trifluoride, zinc chloride, sodium acetate, sodium benzoate, sodium carbonate, calcium oxide and magnesium oxide.

In carrying out process variant (b), the reaction temperatures can be varied within a substantial range. In general, the reaction is carried out at 0° to 150° C., preferably 80° to 120° C.

Substantially equimolar amounts of the reactants are generally used when carrying out process variant (b).

The compounds of the formula (I) may be isolated in the usual manner.

Suitable solvents for the reaction of process variant (c) include all inert organic solvents. Preferred solvents include the solvents mentioned above in connection with process variant (a).

In carrying out process variant (c), the reaction temperatures can be varied within a substantial range. In general, the reaction is carried out at −10° to 70° C., preferably 0° to 40° C.

Suitable solvents for the reaction of process variant (d) include all inert organic solvents. Preferred solvents include the solvents mentioned above in connection with process variant (a).

Catalysts which can be used in process variant (d) include tertiary bases, such as triethylamine and pyridine, or tin-organic compounds, such as dibutyl-tin dilaurate.

In carrying out process variant (d), the reaction temperatures can be varied within a substantial range. In general, the reaction is carried out at 0° to 100° C., preferably 20° to 80° C.

Substantially equimolar amounts of the reactants are generally used when carrying out process variant (d).

To isolate the compounds of the formula (I), the solvent may be distilled off and the residue worked up in accordance with customary methods.

The active compounds according to the invention exhibit a powerful fungitoxic action and a bacteriotoxic action. They do not damage crop plants in the concentrations required for combating fungi and bacteria. For these reasons, they are suitable for use as plant protection agents for combating fungi and bacteria. Fungitoxic agents are employed in plant protection for combating Plasmodiophoromycetes, Oomycetes, Chtridiomycetes, Zygomycetes, Ascomycetes, Basidiomycetes and Deuteromycetes.

The active compounds according to the invention have a broad spectrum of action and can be used against parasitic fungi which attack above-ground parts of plants or attack the plants through the soil, as well as against seed-borne pathogens.

They display particularly good activity against parasitic fungi on above-ground parts of plants, such as species of Erysiphe, species of Podosphaera and species of Venturia, for example against the pathogen of apple scab (*Fusicladium dendriticum*). Furthermore, they exhibit a high activity against cereal diseases, such as against powdery mildew of cereal, and cereal rust.

Furthermore the partially systemic action of the compounds should be pointed out. Thus, it proves possible to protect plants against fungal attack when the active compound is supplied to the above-ground parts of the plant through the soil and through the root.

As plant protection agents, the active compounds according to the invention can be used for the treatment of seed and for the treatment of above-ground parts of plants, especially if the compounds of formula (I) or salts thereof with nontoxic acids are used. They have only a low toxicity to warm-blooded animals and, because of their low odor and their good toleration by the human skin, they are not unpleasant to handle.

When used as seed dressings, the compounds according to the invention are active against seed-borne fungal diseases of plants, both through disinfecting the surface of the seed, for example when combating stripe disease of barley, and systemically, when combating fungal pathogens in the interior of the seed, such as, for example, in the case of loose smuts of wheat and of barley. Furthermore, the seed dressing achieves a systemic protective action against fungal infections of the shoot, for example against mildew.

The active compounds are also suitable for combating animal pests, especially nematodes, which occur in agriculture and in forestry. They are active against normally sensitive and resistant species and against all or some stages of development.

The plant-parasitic nematodes include Pratylenchus spp., *Radopholus similis, Ditylenchus dispaci, Tylenchulus semipenetrans,* Heterodera spp., Meloidogyne spp., Aphelenchoides spp., Longidorus spp., Xiphinema spp. and Trichodorus spp..

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly this purpose: aerosol propellants which are gaseous at normal temperatures and pressures, such as dichlorodifluoromethane and trichlorofluoromethane; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl ar polyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other fungicides and nematicides, or insecticides, acaricides, bactericides, rodenticides, herbicides, fertilizers, growth-regulating agents, bird repellents, plant nutrients, agents for improving soil structure, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1-95% by weight, and preferably 0.5-90% by weight, of the mixture, whereas carrier composition mixtures suitable for direct application or field application generally contemplate those in which the active compound is present in an amount substantially between about 0.00001-10%, preferably 0.0001-1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.00001-95%, and preferably 0.0001-95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50-100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20-100% by weight of the active compound.

Especially when the compounds are used as leaf fungicides, the active compound concentrations in the application forms can be varied within a substantial range. In general, they are from 0.1 to 0.00001% by weight, preferably 0.05 to 0.0001%.

In the treatment of seed, amounts of active compound of 0.001 to 50 g per kilogram of seed preferably 0.01 to 10 g, are generally required.

When the compounds are used as nematicides, the active compound content can be varied within wide ranges. The active compound concentration of the application forms can be from 0.0000001 to 100% by weight of active compound, preferably 0.01 to 10% by weight.

When used against nematodes, the preparations are generally applied to an area of agriculture in amounts of 1 to 100 kg of active compound per hectare, and are then incorporated into the soil.

Furthermore, the present invention contemplates methods of selectively killing, combatting or controlling pests, e.g. fungi and nematodes, which comprises applying to at least one of correspondingly (a) such fungi, (b) such nematodes, and (c) the corresponding habitat thereof, i.e. the locus to be protected, e.g. to a growing crop, to an area where a crop is to be grown or to a domestic animal, a correspondingly combative or toxic amount, i.e. a fungicidally or nematicidally effective amount, of the particular active compound of the invention alone or together with a carrier vehicle as noted above. The instant formulations or compositions are applied in the usual manner, for instance by spraying, atomizing, vaporizing scattering, dusting, watering, squirting, sprinkling, pouring, fumigating, dry dressing, moist dressing, wet dressing, slurry dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

(a) Preparation of the starting material

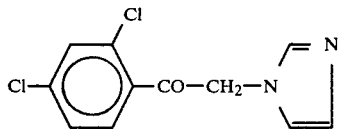

269 g (1 mol) of ω-bromo-2,4-dichloroacetophenone were dissolved in 250 ml of acetonitrile. This solution was added dropwise to a suspension, boiling under reflux, of 69 g (1 mol) of imidazole and 150 g of potassium carbonate in 2 liters of acetonitrile. After heating under reflux for 20 hours, the cooled suspension was filtered, the filtrate was freed from the solvent, the residue was taken up in ethyl acetate and the solution was washed with water, dried over sodium sulphate and freed from the solvent. The residue left from the ethyl acetate solution crystallized out on adding isopropanol. After recrystallization from ligroin/isopropanol, 154 g (60% of theory) of ω-(imidazol-1-yl)-2,4-dichloroacetophenone of melting point 117° C. were obtained.

(b) Preparation of the intermediate

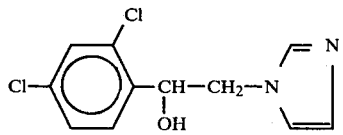

25.5 g (0.1 mol) of ω-(imidazol-1-yl)-2,4-dichloroacetophenone were dissolved in 300 ml of methanol and 4 g (0.1 mol) of sodium borohydride were added incrementally at 5° to 10° C., while stirring. The mixture was then stirred for a further hour at room temperature and was heated to the boil for one hour. After distilling off the solvent, the residue was briefly heated with 200 ml of water and 40 ml of concentrated hydrochloric acid. After having rendered the reaction mixture alkaline with sodium hydroxide solution, the solid reaction product was filtered off. After recrystallization from ligroin/isopropanol, 21.3 g (82% of theory) of 1-(2,4-dichlorophenyl)-1-hydroxy-2-(imidazol-1-yl)-ethane of melting point 90° C. were obtained.

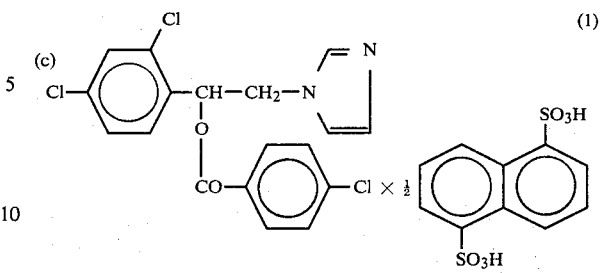

(Process variant (a))

25.8 g (0.1 mol) of 1-(2,4-dichlorophenyl)-1-hydroxy-2-(imidazol-1-yl)-ethane were dissolved in 200 ml of chloroform and the solution was added dropwise, while stirring, to a mixture of 6 g of 80% strength sodium hydride and 100 ml of chloroform. The mixture was then heated for about half an hour under reflux. After it had cooled, 35.4 g (0.2 mol) of 4-chlorobenzoyl chloride were added dropwise, at room temperature, to the sodium salt thus obtained. The mixture was stirred overnight at room temperature, concentrated somewhat, and washed with water. After the mixture had been dried over sodium sulphate, it was concentrated further by distilling off the solvent. 1,5-Naphthalenedisulphonic acid was added to the residue. The resulting crystalline salt was filtered off and dried. 34.4 g (65% of theory) of 1-(4-chlorobenzoyloxy)-1-(2,4-dichlorophenyl)-2-imidazol-1-yl)-ethane naphthalenedisulphonate of melting point 246° C. were obtained.

EXAMPLE 2

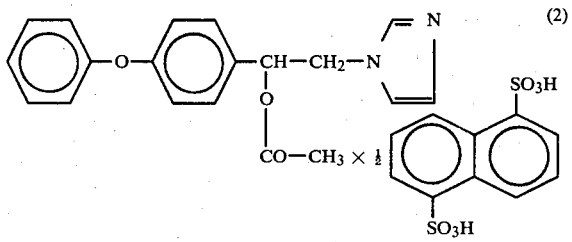

(Process variant (b))

A pinch of sodium acetate was added to 24.5 g (0.088 mol) of 1-hydroxy-2-(imidazol-1-yl)-1-(4-phenoxyphenyl)-ethane in 87.5 mol of acetic anhydride and the mixture was then kept for 10 hours at a temperature of 100° C. Thereafter the solution was cooled and 1,000 ml of water were stirred in. A smeary, crystalline mass precipitated, and this was taken up with chloroform. The chloroform solution was washed with sodium bicarbonate and water, dried over sodium sulphate and concentrated by distilling off the solvent in vacuo. Naphthalenedisulphonic acid was added to the residue. The resulting crystalline salt was filtered off and dried. 28.8 g (70% of theory) of 1-acetoxy-2-(imidazol-1-yl)-(4-phenoxyphenyl)-ethane naphthalenedisulphonate of melting point 193° C. were obtained.

EXAMPLE 3

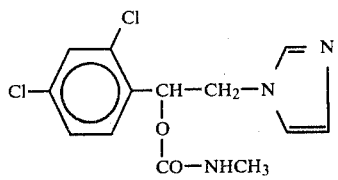
(3)

(Process variant (d))

5.7 g (0.1 mol) of methyl isocyanate and a few drops of dibutyl-tin dilaurate were added to 25.8 g (0.1 mol) of 1-(2,4-dichlorophenyl)-1-hydroxy-2-(imidazol-1-yl)-ethane in 250 ml of benzene, while stirring. The mixture was stirred overnight at 60°–65° C. It was then allowed to cool and the crystalline precipitate was filtered off and rinsed with ether. 25.5 g (81% of theory) of 1-(2,4-dichlorophenyl)-2-(imidazol-1-yl)-methylcarbamoyloxy-ethane of melting point 106°–108° C. were obtained.

EXAMPLE 4

(a) Preparation of the starting material:

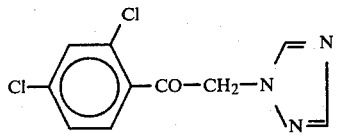

269 g (1 mol) of ω-bromo-2,4-dichloroacetophenone were dissolved in 250 ml of acetonitrile. This solution was added dropwise to a suspension, boiling under reflux, of 69 g (1 mol) of 1,2,4-triazole and 150 g of potassium carbonate in 2 liters of acetonitrile. After heating the mixture under reflux for 20 hours, the suspension was allowed to cool and was then filtered, the filtrate was freed from the solvent, the residue was taken up in ethyl acetate and the solution was washed with water, dried over sodium sulphate and freed from the solvent. The residue from the ethyl acetate crystallized out on adding isopropanol. After recrystallization from ligroin/isopropanol, 154 g (60% of theory) of ω-(1,2,4-triazol-1-yl)-2,4-dichloroacetophenone of melting point 117° C. were obtained.

(b) Preparation of the intermediate:

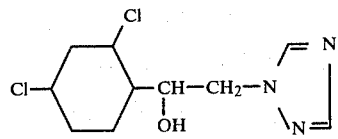

25.6 g (0.1 mol) of ω-(1,2,4-triazol-1-yl)-2,4-dichloroacetophenone were dissolved in 300 ml of methanol and 4 g (0.1 mol) of sodium borohydride were added in portions at 5° to 10° C., while stirring. The mixture was then stirred for a further hour at room temperature, and heated to the boil for one hour. After distilling off the solvent, the residue was briefly heated with 200 ml of water and 40 ml of concentrated hydrochloric acid. After having rendered the reaction mixture alkaline with sodium hydroxide solution, the solid reaction product was filtered off. After recrystallization from ligroin/isopropanol, 21.3 g (82% of theory) of 1-hydroxy-1-(2,4-dichlorophenyl)-2-(1,2,4-triazol-1-yl)-ethane of melting point 90° C. were obtained.

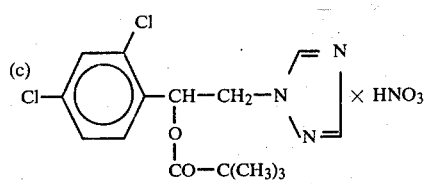
(4)

(Process variant (a))

25.8 g (0.1 mol) of 1-(2,4-dichlorophenyl)-1-hydroxy-2-(1,2,4-triazol-1-yl)-ethane were dissolved in 200 ml of dioxane and the solution was added dropwise, while stirring, to a mixture of 6 g of 80% strength sodium hydride and 100 ml of dioxane. The mixture was then heated for about half an hour under reflux. After it had cooled, 24 g (0.2 mol) of trimethylacetic acid chloride in 100 l of dioxane were added dropwise, at room temperature, to the sodium salt obtained as above. The mixture was stirred overnight at room temperature and was concentrated by distilling off the solvent in vacuo, and the residue was taken up in chloroform. The chloroform solution was washed with water, dried over sodium sulphate and again concentrated. 100 ml of chloroform were added to the residue, followed by 5 ml of nitric acid added while cooling with ice. The precipitation of the nitrate was completed by adding ether. The mixture was filtered and the residue was dried. 19.4 g (48% of theory) of 1-(2,4-dichlorphenyl)-1-trimethylacetoxy-2-(1,2,4-triazol-1-yl)-ethane nitrate of melting point 149°–151° C. were obtained.

EXAMPLE 5

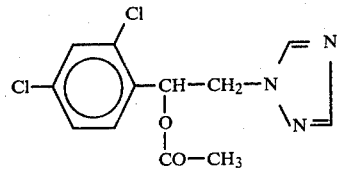
(5)

(Process variant (b))

A pinch of sodium acetate was added to 25.8 g (0.1 mol) of 1-(2,4-dichlorophenyl)-1-hydroxy-2-(1,2,4-triazol-1-yl)-ethane in 100 ml of acetic anhydride and the mixture was then kept for 10 hours at a temperature of 100° C. Thereafter the solution was cooled and stirred into 1,000 ml of water. A smeary, crystalline mass precipitated, which was taken up in chloroform. The chloroform solution was washed with sodium bicarbonate and water, dried over sodium sulphate and concentrated by distilling off the solvent in vacuo. The residue crystallized on adding petroleum ether. 13 g (43% of theory) of 1-acetoxy-1-(2,4-dichlorophenyl)-2-(1,2,4-triazol-1-yl)-ethane of melting point 92°–96° C. were obtained.

EXAMPLE 6

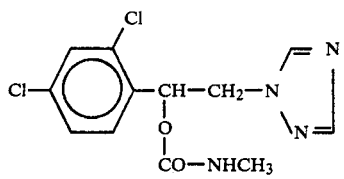

(6)

(Process variant (d))

5.7 g (0.1 mol) of methyl isocyanate and a few drops of dibutyl-tin dilaurate were added, while stirring, to 25.8 g (0.1 mol) of 1-(2,4-dichlorophenyl)-1-hydroxy-2-(1,2,4-triazol-1-yl)-ethane in 250 ml of ethyl acetate. The mixture was stirred overnight at 60°–65° C. It was then allowed to cool and the crystalline precipitate was filtered off and washed with ether. 30.4 g (97% of theory) of 1-(2,4-dichlorophenyl)-1-methylcarbamoyloxy-2-(1,2,4-triazol-1-yl)-ethane of melting point 204° C. were obtained.

The following can be obtained by procedures analogous to those of the above examples:

TABLE 1

Structure (I):

$R_n$-phenyl-CH(O-CO-R')-CH$_2$-N(triazole/tetrazole ring with A)

| Compound No. | $R_n$ | R' | A | Melting point (°C.) |
|---|---|---|---|---|
| 7 | 2,4-Cl$_2$ | NH$_2$ | CH | 125 |
| 8 | 4-C$_6$H$_5$ | —NH—CH$_3$ | CH | 182 |
| 9 | 4-C$_6$H$_5$ | CH$_3$ | CH | 328 (× ½ naphthalene-1,5-disulfonic acid) |
| 10 | 4-(4-Cl-C$_6$H$_4$) | CH$_3$ | CH | 274 (× ½ naphthalene-1,5-disulfonic acid) |
| 11 | 2,4-Cl$_2$ | CH$_3$ | CH | 223 (× ½ naphthalene-1,5-disulfonic acid) |
| 12 | 4-O-(4-Cl-C$_6$H$_4$) | CH$_3$ | CH | 200 (× ½ naphthalene-1,5-disulfonic acid) |
| 13 | 2,4-Cl$_2$ | N(CH$_3$)$_2$ | N | 140 |
| 14 | 2,4-Cl$_2$ | C$_2$H$_5$ | N | 150 (× ½ naphthalene-1,5-disulfonic acid) |
| 15 | 2,4-Cl$_2$ | CH$_2$Cl | N | 227 (× ½ naphthalene-1,5-disulfonic acid) |
| 16 | 4-(4-Cl-C$_6$H$_4$) | CH$_3$ | N | 123 |

TABLE 1-continued $$\underset{R_n}{\underset{|}{\text{C}_6H_4}}\text{CH—CH}_2\text{—N}\genfrac{}{}{0pt}{}{\diagup\text{N}}{\diagdown_A=}$$
with O—CO—R' on CH (I)

| Compound No. | $R_n$ | R' | A | Melting point (°C.) |
|---|---|---|---|---|
| 17 | 2,4-Cl$_2$ | —C$_6$H$_4$—Cl | N | 174 (× ½ naphthalene-1,5-disulfonic acid) |
| 18 | 4-O—C$_6$H$_4$—Cl | CH$_3$ | N | 150 (× HNO$_3$) |
| 19 | 2,4-Cl$_2$ | —NH—C$_6$H$_5$ | N | 143 |
| 20 | 2,4-Cl$_2$ | —N(CH$_3$)COCH$_3$ | N | 120 |
| 21 | 4—C$_6$H$_4$—Cl | —NHCH$_3$ | N | 180 |
| 22 | 2,4-Cl$_2$ | —C$_6$H$_3$(Cl)$_2$ (3,4) | N | 205 (× ½ naphthalene-1,5-disulfonic acid) |
| 23 | 2,4-Cl$_2$ | NH$_2$ | N | 164 |
| 24 | 2,4-Cl$_2$ | —NH—C$_6$H$_3$(Cl)$_2$ (2,4) | N | 125 |
| 25 | 2,4-Cl$_2$ | NH—C$_6$H$_5$ | CH | 223 (× ½ naphthalene-1,5-disulfonic acid) decompos. |
| 26 | 4—C$_6$H$_4$—Cl | C(CH$_3$)$_3$ | N | 121 |
| 27 | 4—C$_6$H$_4$—Cl | —NH—C$_6$H$_5$ | N | 170 decompos. |
| 28 | 4-Cl | CH$_3$ | N | 90–92 |
| 29 | 4-Cl | C(CH$_3$)$_3$ | N | 135–136 |
| 30 | 4-Cl | —NH—CH$_3$ | N | 177–180 |
| 31 | 4—C$_6$H$_4$—Cl | —NH—C$_6$H$_3$(Cl)$_2$ (3,5) | N | 116–126 |
| 32 | 4-Cl | —N(CH$_3$)COCH$_3$ | N | 155–158 (× HCl) |

TABLE 1-continued $$R_n\text{-Ph-CH(O-CO-R')-CH}_2\text{-N} \diagup \text{azole (A=N or CH)} \quad (I)$$

| Compound No. | $R_n$ | R' | A | Melting point (°C.) |
|---|---|---|---|---|
| 33 | 2,4-Cl$_2$ | (cyclohexyl, H) | N | 170–175 (× HCl) |
| 34 | 2,4-Cl$_2$ | CHCl$_2$ | N | 128–130 |
| 35 | 4-Cl | —NH—(3,4-Cl$_2$-phenyl) | N | 180–185 |

Other compounds which can be similarly prepared include:

TABLE 2

| $R_n$ | $R^1$ | A |
|---|---|---|
| 2,4,6-F$_3$ | —CH$_2$—CH=CH$_2$ | N |
| 4-Br—2-CH$_3$— | —CH$_2$—C≡CH | N |
| 3-NO$_2$ | ClF$_2$C— | CH |
| 3-CN | phenyl- | CH |
| 4-C$_2$H$_5$ | phenyl-CH$_2$ | N |
| 4-H$_3$CSO$_2$— | phenyl-O—CH$_2$—CH$_2$— | N |
| 4-CH$_3$O— | phenyl | N |
| 4-C$_2$H$_5$S— | NC-phenyl-CH$_2$—CH$_2$— | N |
| 4-CF$_2$ClC— | O$_2$N-phenyl-O—CH$_2$— | N |
| 2-F-phenyl | H$_3$C-phenyl-CH$_2$ | N |
| Br-phenyl-O— | CH$_3$ | N |
| NC-phenyl- | CH$_3$ | N |
| O$_2$N-phenyl- | CH$_3$ | N |
| FCl$_2$C-phenyl- | CH$_3$ | N |

The activity of the novel compounds is illustrated by the following comparative examples wherein the known comparison compounds are identified as follows:

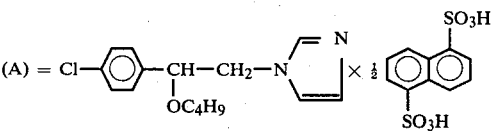

(A) = Cl—phenyl—CH(OC$_4$H$_9$)—CH$_2$—N(azole) × ½ naphthalene-1,5-disulfonic acid

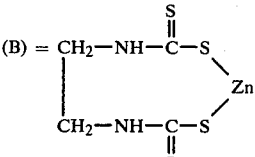

(B) = zinc ethylenebis(dithiocarbamate)

EXAMPLE 7

Seed dressing test/stripe disease of barley (seed-borne mycosis)

To produce a suitable dry dressing, the active compound was extended with a mixture of equal parts by weight of talc and kieselguhr to give a finely powdered mixture with the desired concentration of active compound.

To apply the dressing, barley seed, which had been naturally infected by *Drechslera graminae* (Reb. ex Schlect.) Ito (previously *Helminthosporium gramineum*), were shaken with the dressing in a closed glass flask. The seed, on moist filter paper discs in closed Petri dishes, was exposed to a temperature of 4° C. for 10 days in a refrigerator. The germination of the barley, and possibly also of the fungus spores, was thereby initiated. Two batches of 50 grains of the pregerminated barley were subsequently sown 2 cm deep in Fruhstorfer standard soil and cultivated in a greenhouse at temperatures of about 18° C. in seed boxes which were exposed to light for 16 hours daily. The typical symptoms of the stripe disease developed within 3 to 4 weeks.

After this time, the number of diseased plants was determined as a percentage of the total number of emerged plants. The fewer plants were diseased, the more effective was the active compound.

The active compounds, the concentrations of the active compounds in the dressing, the amounts of dressing used and the number of diseased plants can be seen from Table 2;

TABLE 3

Seed dressing test/stripe disease of barley

| Active compound | Amount of dressing | Number of plants with |

| Active compound | concentration in the dressing in % by weight | used in g/kg of seed | stripe disease, as % of the emerged plants |
|---|---|---|---|
| Without dressing | — | — | 54.4 |
| (B) | 25 | 2 | 27.8 |
| (12) | 25 | 2 | 2.3 |

EXAMPLE 8

Mycelium growth test

Nutrient medium used:
20 parts by weight of agar-agar
200 parts by weight of potato decoction
5 parts by weight of malt
15 parts by weight of dextrose
5 parts by weight of peptone
2 parts by weight of disodium hydrogen phosphate
0.3 part by weight of calcium nitrate
Composition of the solvent mixture
0.19 part by weight of acetone
0.01 part by weight of emulsifier (alkylaryl polyglycol ether)
1.80 parts by weight of water
Ratio of solvent mixture to nutrient medium:
2 parts by weight of solvent mixture
100 parts by weight of agar nutrient medium The amount of active compound required for the desired active compound concentration in the nutrient medium was mixed with the stated amount of solvent. The concentrate was thoroughly mixed, in the stated proportion, with the liquid nutrient medium which had been cooled to 42° C. and was then poured into Petri dishes of 9 cm diameter. Control plates to which the preparation had not been added were also set up.

When the nutrient medium had cooled and solidified, the plates were inoculated with the species of fungi stated in the table and incubated at about 21° C.

Evaluation was carried out after 4–10 days, dependent upon the speed of growth of the fungi. When evaluation was carried out the radial growth of the mycelium on the treated nutrient media was compared with the growth on the control nutrient medium. In the evaluation of the fungus growth, the following characteristic values were used:

1 no fungus growth
up to 3 very strong inhibition of growth
up to 5 medium inhibition of growth
up to 7 slight inhibition of growth
9 growth equal to that of untreated control The active compounds, the active compound concentrations and the results can be seen from Table 4:

TABLE 4

Mycelium growth test
Fungi and 1 bacterium
Active compound concentration 10 ppm

| Active compounds | Fusarium culmorum | Sclerotinia sclerotiorum | Fusarium nivale | Colletotrichum coffeanum | Rhizoctonia solani | Pythium ultimum | Cochliobolus miyabeanus | Botrytis cinerea | Verticillium alboatrum | Pyricularia oryzae | Phialophora cinerescens | Helminthosporium gramineum | Mycosphaerella musicola | Phytophthora cactorum | Pellicutlaria sasakii | Xanthomonas oryzae |
|---|---|---|---|---|---|---|---|---|---|---|---|---|---|---|---|---|
| (B) | 9 | 9 | 9 | 9 | 9 | 5 | 9 | 9 | 9 | 9 | 9 | 5 | 5 | 9 | 9 | 9 |
| (2) | — | 3 | — | — | 3 | 1 | 1 | 3 | 3 | 5 | 1 | 1 | — | 1 | 1 | — |
| (9) | 5 | 3 | 5 | 5 | 5 | 1 | 1 | 1 | 3 | 5 | 1 | 1 | 1 | — | 1 | — |
| (10) | 5 | 1 | 3 | 3 | 3 | 1 | 1 | 1 | — | 1 | 5 | 1 | 1 | — | 1 | — |
| (1) | 5 | 1 | 5 | 5 | 1 | 2 | 1 | 1 | 1 | — | 3 | 1 | 1 | 1 | 1 | 1 |

EXAMPLE 9

Nematocides/critical concentration test

Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil, which is given in ppm, was decisive. The soil was filled into pots, lettuce was sown in and the pots were kept at a greenhouse temperature of 27° C.

After 4 weeks, the lettuce roots were examined for infestation with nematodes (root galls), and the degree of effectiveness of the active compound was determined as a percentage. The degree of effectiveness is 100% when infestation was completely avoided; it is 0% when the infestation was exactly the same as in the case of control plants in untreated soil which had been infested in the same manner.

The active compound, the amounts applied and the results can be seen from Table 5:

TABLE 5

Nematicides

| Active compound | Degree of destruction in % at an active compound concentration of 20 ppm |
|---|---|
| (A) | 0 |
| (3) | 100 |
| (7) | 100 |
| (8) | 100 |
| (2) | 100 |
| (9) | 100 |
| (10) | 100 |
| (11) | 100 |
| (1) | 100 |
| (4) | 100 |
| (14) | 100 |
| (15) | 100 |

TABLE 5-continued

| | Nematicides |
|---|---|
| Active compound | Degree of destruction in % at an active compound concentration of 20 ppm |
| (16) | 100 |
| (17) | 100 |
| (6) | 100 |
| (19) | 100 |
| (20) | 100 |

EXAMPLE 10

Fusicladium test (apple)/(protective)

Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated additions.

Young apple seedlings in the 4-6 leaf stage were sprayed with the spray liquid until dripping wet. The plants remained in a greenhouse for 24 hours at 20° C. and at a relative atmospheric humidity of 70%. They were then inoculated with an aqueous conidium suspension of the apple scab causative organism (*Fusicladium dendriticum*) and incubated for 18 hours in a humidity chamber at 18°-20° C. and at a relative atmospheric humidity of 100%.

The plants were then brought into a greenhouse again for 14 days.

15 days after inoculation, the infection of the seedlings was determined. The assessment data were converted to percent infection. 0% means no infection; 100% means that the plants were totally infected.

The active compounds, the concentrations of the active compounds and the results can be seen from Table 6:

TABLE 6

| | Fusicladium Test (Apple)/protective |
|---|---|
| Active compound | Infection in % at an active compound concentration of (by weight) 0.00025% |
| (A) | 19 |
| (4) | 5 |
| (16) | 17 |

EXAMPLE 11

Erysiphe test (cucumbers)/protective

Solvent: 4.7 parts by weight of acetone
Emulsifier: 0.3 part by weight of alkylaryl polyglycol ether
Water: 95 parts by weight.

The amount of the active compound required for the desired concentration of active compound in the spray liquid was mixed with the stated amount of solvent and the concentration was diluted with the stated amount of water containing the stated additions.

Young cucumber plants with about three foliage leaves were sprayed with the spray liquid until dripping wet. The cucumber plants remained in a greenhouse for 24 hours to dry. They were then, for the purpose of inoculation, dusted with conidia of the fungus *Erysiphe cichoriacearum*. The plants were subsequently placed in a greenhouse at 23°-24° C. and at a relative atmospheric humidity of about 75%.

After 12 days, the infection of the cucumber plants was determined. The assessment data were converted to percent infection. 0% means no infection; 100% means that the plants were totally infected.

The active compounds, the concentrations of the active compounds and the results can be seen from Table 7:

TABLE 7

| | Erysiphe Test (cucumbers)/protective | |
|---|---|---|
| | Infection in % at an active compound concentration of (by weight) | |
| Active compound | 0.00062% | 0.0005% |
| (A) | 62 | — |
| (3) | 50 | — |
| (7) | 46 | — |
| (11) | — | 59 |
| (1) | — | 16 |
| (13) | 25 | — |
| (5) | — | 19 |
| (4) | — | 0 |
| (14) | — | 34 |
| (15) | — | 34 |
| (19) | — | 0 |

EXAMPLE 12

Shoot treatment test/cereal mildew/protective
(leaf-destructive mycosis)

To produce a suitable preparation of active compound, 0.25 part by weight of active compound was taken up in 25 parts by weight of dimethylformamide and 975 parts by weight of water were added. The concentrate was diluted with water to the desired final concentration of the spray liquor.

To test for protective activity, single-leaved young barley plants of the Amsel variety were sprayed with the preparation of active compound until dew-moist. After drying, the barley plants were dusted with spores of *Erysiphe graminis* var.*hordei*.

After 6 days' dwell time of the plants at a temperature of 21°-22° C. and 80-90% atmospheric humidity the occurrence of mildew pustules on the plants was evaluated. The degree of infection was expressed as a percentage of the infection of the untreated control plants. 0% denoted no infection and 100% denoted the same degree of infection as in the case of the untreated control. The active compound was the more active, the lower was the degree of mildew infection.

The active compounds, active compound concentrations in the spray liquor and degrees of infection can be seen from Table 8:

TABLE 8

| Shoot treatment test/cereal mildew/ protective | | |
|---|---|---|
| Active compound | Active compound concentration in the spray liquor in % by weight | Infection in % of that of the untreated control |
| Untreated | — | 100.0 |
| (B) | 0.025 | 100.0 |
| (3) | 0.025 | 16.3 |
| (7) | 0.025 | 17.5 |

TABLE 8-continued

Shoot treatment test/cereal mildew/protective

| Active compound | Active compound concentration in the spray liquor in % by weight | Infection in % of that of the untreated control |
|---|---|---|
| (2) | 0.025 | 16.3 |
| (10) | 0.025 | 51.3 |
| (11) | 0.025 | 18.8 |
| (1) | 0.025 | 25.0 |
| (12) | 0.025 | 25.0 |
| (13) | 0.025 | 0.0 |
| (5) | 0.025 | 0.0 |
| (4) | 0.025 | 0.0 |
| (14) | 0.025 | 0.0 |
| (15) | 0.025 | 0.0 |
| (17) | 0.025 | 12.5 |
| (20) | 0.025 | 5.0 |
| (21) | 0.025 | 66.3 |

EXAMPLE 13

Powdery mildew of barley (*Erysiphe graminis* var. *hordei*)/systemic (fungal disease of cereal shoots)

The active compounds were used as pulverulent seed treatment agents. They were prepared by extending the particular active compound with a mixture of equal parts by weight of talc and kieselguhr to give a finely pulverulent mixture of the desired concentration of active compound.

For the treatment of seed, barley seed was shaken with the mixture of active compound and extender in a closed glass bottle. The seed was sown at the rate of 3×12 grains in flowerpots, 2 cm deep in a mixture of one part by volume of Fruhstorfer standard soil and one part by volume of quartz sand. The germination and emergence took place under favorable conditions in a greenhouse. 7 days after sowing, when the barley plants had developed their first leaf, they were dusted with fresh spores of *Erysiphe graminis* var. *hordei* and grown on at 21°–22° C. and 80–90% relative atmospheric humidity and 16 hours' exposure to light. The typical mildew postules formed on the leaves over the course of 6 days.

The degree of infection is expressed as a percentage of the infection of the untreated control plants. Thus, 0% denotes no infection and 100% denotes the same degree of infection as in the case of the untreated control. The active compound is the more active, the lower is the degree of mildew infection.

The active compounds and concentrations of active compound in the seed treatment agent, as well as the amount used of the latter, and the percentage infection with mildew can be seen from Table 9:

TABLE 9

Barley mildew test (*Erysiphe graminis* var. *hordei*)/systemic

| Active compound | Active compound in the dressing in % by weight | Amount of dressing used in g/kg of seed | Infection in % of that of the untreated control |
|---|---|---|---|
| without dressing | — | — | 100.0 |
| (B) | 25 | 10 | 100.0 |
| (5) | 25 | 10 | 0.0 |
| (4) | 25 | 10 | 0.0 |

TABLE 9-continued

Barley mildew test (*Erysiphe graminis* var. *hordei*)/systemic

| Active compound | Active compound in the dressing in % by weight | Amount of dressing used in g/kg of seed | Infection in % of that of the untreated control |
|---|---|---|---|
| (14) | 25 | 10 | 0.0 |
| (15) | 25 | 10 | 0.0 |
| (17) | 25 | 10 | 0.0 |
| (19) | 25 | 10 | 78.8 |
| (20) | 25 | 10 | 8.8 |
| (21) | 25 | 10 | 50.0 |

EXAMPLE 14

Shoot treatment test/cereal rust/protective (leaf-destructive mycosis)

To produce a suitable preparation of active compound, 0.25 part by weight of active compound was taken up in 25 parts by weight of dimethylformamide and 975 parts by weight of water were added. The concentrate was diluted with water to the desired final concentration of the spray liquor.

To test the protective activity, one-leaved young wheat plants of the Michigan Amber variety were inoculated with uredospore suspension of *Puccinia recondita* in 0.1% strength aqueous agar. After the spore suspension had dried on, the wheat plants were sprayed with the preparation of active compound until dew-moist and were placed, for incubation, in a greenhouse for 24 hours at about 20° C. and 100% relative atmospheric humidity.

After 10 days' dwell time of the plants at a temperature of 20° C. and 80–90% atmospheric humidity, the occurrence of rust pustules on the plant was evaluated. The degree of infection was expressed as a percentage of the infection of the untreated control plants. 0% denotes no infection and 100% denotes the same degree of infection as in the case of the untreated control. The active compound is the more active, the lower is the degree of rust infection.

The active compounds, active compound concentrations in the spray liquor and degrees of infection can be seen from Table 10:

TABLE 10

Shoot treatment test/Cereal rust/protective

| Active compound | Active compound concentration in the spray liquor in % by weight | Infection in % of that of the untreated control |
|---|---|---|
| Untreated | — | 100.0 |
| (B) | 0.25 | 93.8 |
| (10) | 0.025 | 0.0 |
| (1) | 0.025 | 50.0 |
| (12) | 0.025 | 41.3 |
| (5) | 0.025 | 72.5 |
| (4) | 0.025 | 25.0 |
| (14) | 0.025 | 75.0 |
| (16) | 0.025 | 50.0 |
| (21) | 0.025 | 50.0 |

It will be appreciated that the instant specification and examples are set forth by way of illustration and not limitation, and that various modifications and changes may be made without departing from the spirit and scope of the present invention.

What is claimed is:
1. A 1-acyloxy-1-phenyl-2-azolyl-ethane or salt thereof, the 1-acyloxy-1-phenyl-2-azolyl-ethane being of the formula

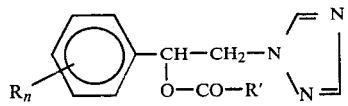

in which
- R is halogen; alkyl with 1 to 4 carbon atoms; alkoxy with 1 or 2 carbon atoms; alkylthio with 1 or 2 carbon atoms; alkylsulphonyl with 1 to 4 carbon atoms; haloalkyl with up to 4 carbon atoms; nitro; cyano; phenyl; phenoxy; or phenyl or phenoxy substituted by fluorine, chlorine, bromine, cyano, nitro or haloalkyl with 1 or 2 carbon atoms and up to 3 fluorine plus chlorine atoms;
- R' is alkyl with 1 to 6 carbon atoms; alkenyl with 2 to 4 carbon atoms; alkynyl with 2 to 4 carbon atoms; cycloalkyl with 5 to 7 carbon atoms; haloalkyl with 1 or 2 carbon atoms; phenyl; phenylalkyl or phenoxyalkyl each with 1 or 2 carbon atoms in the alkyl moiety; such phenyl, phenylalkyl or phenoxyalkyl substituted on the phenyl by halogen, amino, cyano, nitro or alkyl with 1 or 2 carbon atoms; amino; alkylamino, dialkylamino or alkylalkylcarbonylamino with 1 or 2 carbon atoms in each alkyl moiety; phenylamino; or phenylamino substituted by halogen, nitro or cyano; and
- n represents 0, 1, 2, 3, 4 or 5.

2. A compound according to claim 1 in which R is fluorine, chlorine, bromine, nitro, cyano, alkyl or alkylsulphonyl each with 1 or 2 carbon atoms, haloalkyl with up to 2 carbon atoms and up to 3 chlorine plus fluorine atoms, phenyl, phenoxy, or phenyl or phenoxy substituted by fluorine, chlorine, bromine, cyano, nitro or haloalkyl with 1 or 2 carbon atoms and up to 3 fluorine plus chlorine atoms; R' is alkyl with 1 to 4 carbon atoms, alkenyl or alkynyl with 2 to 4 carbon atoms, haloalkyl with 1 or 2 carbon atoms and 1 to 5 fluorine plus chlorine atoms, cycloalkyl with 5 to 7 carbon atoms, amino, alkylamino or dialkylamino or alkyl-alkylcarbonylamino each with 1 or 2 carbon atoms in each alkyl moiety, phenylamino optionally substituted by halogen, nitro or cyano, phenylalkyl or phenoxyalkyl each with 1 or 2 carbon atoms in the alkyl moiety, or phenyl or such phenylalkyl or phenoxyalkyl substituted on the phenyl by halogen, amino, cyano, nitro or alkyl with 1 or 2 carbon atoms; and n is 0, 1, 2 or 3.

3. The compound according to claim 1 wherein the compound is 1-(2,4-dichlorophenyl)-1-trimethylacetoxy-2-(1,2,4-triazol-1-yl)-ethane of the formula

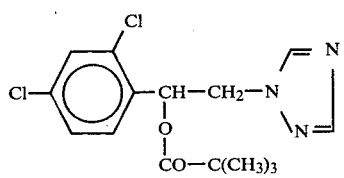

4. The compound according to claim 1 wherein the compound is 1-(2,4-dichlorophenyl)-1-acetoxy-2-(1,2,4-triazol-1-yl)-ethane of the formula

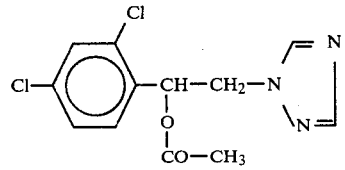

5. The compound according to claim 1 wherein the compound is 1-(2,4-dichlorophenyl)-1-methylcarbamoyloxy-2-(1,2,4-triazol-1-yl)-ethane of the formula

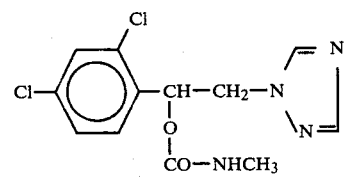

6. The compound according to claim 1 wherein the compound is 1-(2,4-dichlorophenyl)-1-(N-acetyl-N-methyl-carbamoyloxy)-2-(1,2,4-triazol-1-yl)-ethane of the formula

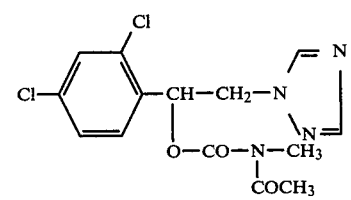

7. A compound according to claim 1 in which R is nitro, cyano, alkyl or alkyl-sulphonyl each with 1 or 2 carbon atoms, haloalkyl with up to 2 carbon atoms and up to 3 chlorine plus fluorine atoms, phenyl, phenoxy, or phenyl or phenoxy substituted by fluorine, chlorine, bromine, cyano, nitro or haloalkyl with 1 or 2 carbon atoms and up to 3 fluorine plus chlorine atoms; R' is alkenyl or alkynyl with 2 to 4 carbon atoms, haloalkyl with 1 or 2 carbon atoms and 1 to 5 fluorine plus chlorine atoms, cycloalkyl with 5 to 7 carbon atoms, amino, alkylamino or dialkylamino or alkyl-alkylcarbonylamino each with 1 or 2 carbon atoms in each alkyl moiety, phenylamino optionally substituted by halogen, nitro or cyano, phenylalkyl or phenoxyalkyl each with 1 or 2 carbon atoms in the alkyl moiety, or phenyl or such phenylalkyl or phenoxyalkyl substituted on the phenyl by halogen, amino, cyano, nitro or alkyl with 1 or 2 carbon atoms; and n is 1, 2 or 3.

8. The compound according to claim 1 wherein the compound is 1-(2,4-dichlorophenyl)-1-dichloroacetoxy-2-(1,2,4-triazol-1-yl)-ethane of the formula

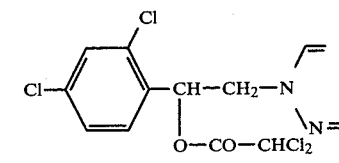

9. The compound according to claim 1 wherein the compound is 1-(4-chlorophenyl)-1-[N-(2,4-dichlorophenyl)-carbamoyloxy]-2-(1,2,4-triazol-1-yl)-ethane of the formula

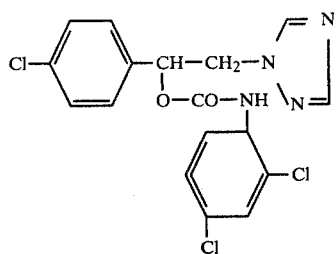

10. A fungicidial, bactericidal or nematicidal composition containing as active ingredient a fungicidally, bactericidally or nematocidally effective amount of a compound according to claim 1, in admixture with a diluent.

11. A method of combating fungus, bacterium or nematode pests which comprises applying to the pests or a habitat thereof a fungicidally, bactericidally or nematicidally effective amount of a compound according to claim 1.

12. The method according to claim 11 in which said compound is 1-(2,4-dichlorophenyl)-1-trimethyl-acetoxy-2-(1,2,4-triazol-1-yl)-ethane, 1-(2,4-dichlorophenyl)-1-acetoxy-2-(1,2,4-triazol-1-yl)-ethane, 1-(2,4-dichlorophenyl)-1-methylcarbamoyloxy-2-(1,2,4-triazol-1-yl)-ethane, 1-(2,4-dichlorophenyl)-1-(N-acetyl-N-methyl-carbamoyloxy)-2-(1,2,4-triazol-1-yl)-ethane, 1-(2,4-dichlorophenyl)-1-dichloroacetoxy-2-(1,2,4-triazol-1-yl)-ethane or 1-(4-chlorophenyl)-1-[N-(2,4-dichlorophenyl)-carbamoyloxy]-2-(1,2,4-triazol-1-yl)-ethane.

13. A 1-acyloxy-1-phenyl-2-azolyl-ethane or salt thereof, the 1-acyloxy-1-phenyl-2-azolyl-ethane being of the formula

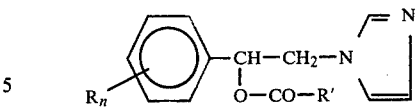

in which
R is phenyl substituted by fluorine, chlorine or bromine, or phenoxy substituted by fluorine, chlorine or bromine;
R' is alkyl with 1 to 6 carbon atoms; alkenyl with 2 to 4 carbon atoms; alkynyl with 2 to 4 carbon atoms; cycloalkyl with 5 to 7 carbon atoms; haloalkyl with 1 or 2 carbon atoms; phenyl; phenylalkyl or phenoxyalkyl each with 1 or 2 carbon atoms in the alkyl moiety; such phenyl, phenylalkyl or phenoxyalkyl substituted on the phenyl by halogen, amino, cyano, nitro or alkyl with 1 or 2 carbon atoms; amino; alkylamino, dialkylamino or alkylalkylcarbonylamino with 1 or 2 carbon atoms in each alkyl moiety; phenylamino; or phenylamino substituted by halogen, nitro or cyano; and
n represents 1, 2 or 3.

14. The compound according to claim 13 wherein the compound is 1-[4-(4'-chlorophenyl)-phenyl]-1-acetoxy-2-(imidazol-1-yl)-ethane of the formula

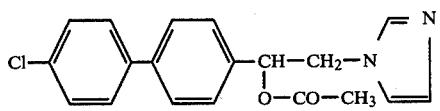

15. A fungicidial, bactericidal or nematicidal composition containing as active ingredient a fungicidally, bactericidally or nematicidally effective amount of a compound according to claim 13, in admixture with a diluent.

16. A method of combating fungus, bacterium or nematode pests which comprises applying to the pests or a habitat thereof a fungicidally, bactericidally or nematicidally effective amount of a compound according to claim 13.

* * * * *

UNITED STATES PATENT AND TRADEMARK OFFICE
CERTIFICATE OF CORRECTION

PATENT NO. : 4,349,556
DATED : September 14, 1982
INVENTOR(S) : Helmut Timmler et al It is certified that error appears in the above—identified patent and that said Letters Patent is hereby corrected as shown below:

| | |
|---|---|
| Col. 9, line 4 | Delete "dispaci" and insert --dipsaci-- |
| Col. 14, line 24 | Delete "1" and insert --ml-- |
| Col. 20, line 49 | Delete "Reb" and insert --Rab-- |
| Table 4 (second to last col.) | Delete "Pellicutlaria" and insert --Pellicularia-- |

Signed and Sealed this

Eighteenth Day of January 1983

[SEAL]

Attest:

GERALD J. MOSSINGHOFF

Attesting Officer

Commissioner of Patents and Trademarks